US005677396A

United States Patent [19]
Klang

[11] Patent Number: 5,677,396
[45] Date of Patent: Oct. 14, 1997

[54] POLYETHERESTER RESINS FROM DIOL DIESTERS

[75] Inventor: Jeffrey A. Klang, Exton, Pa.

[73] Assignee: ARCO Chemical Technology, L.P., Greenville, Del.

[21] Appl. No.: 619,059

[22] Filed: Mar. 20, 1996

[51] Int. Cl.$^6$ .............................. C08F 20/00; C08G 63/02

[52] U.S. Cl. .......................... 525/445; 528/272; 528/275; 528/281; 528/296; 528/300; 528/302; 528/303; 525/10; 525/11; 525/437; 525/444; 525/445; 525/447; 525/448; 523/500

[58] Field of Search ..................................... 528/272, 296, 528/300, 302, 303, 275, 281; 525/10, 11, 437, 444, 445, 447, 448; 523/500

[56] References Cited

U.S. PATENT DOCUMENTS

| 5,319,006 | 6/1994 | Yang et al. | 523/500 |
| 5,436,313 | 7/1995 | Klang et al. | 528/274 |
| 5,436,314 | 7/1995 | Yang et al. | 528/274 |
| 5,569,737 | 10/1996 | Yang et al. | 528/274 |
| 5,610,205 | 3/1997 | Yang et al. | 522/102 |
| 5,612,444 | 3/1997 | Cai et al. | 528/274 |

Primary Examiner—Samuel A. Acquah
Attorney, Agent, or Firm—Jonathan L. Schuchardt

[57] ABSTRACT

An improved process for making polyetherester resins is disclosed. The process comprises reacting a polyether with a diol diester in the presence of a catalyst that promotes random insertion of the diester into carbon-oxygen bonds of the polyether to produce the polyetherester resin. The process of the invention offers many advantages, including higher resin yields, reduced by-product generation, and the ability to make resins with low color and low acid numbers. The resins are useful for making polyetherester thermosets.

25 Claims, No Drawings

POLYETHERESTER RESINS FROM DIOL DIESTERS

FIELD OF THE INVENTION

The invention relates to polyetherester resins. In particular, the invention is an improved process for making polyetherester resins from diol diesters and polyether polyols. The resins are valuable intermediates for making polyetherester thermosets.

BACKGROUND OF THE INVENTION

Recently, we described a new process for making polyetherester resins from polyethers (see U.S. Pat. No. 5,319,006). The process reacts a polyether with a cyclic anhydride (such as maleic anhydride) in the presence of a Lewis acid catalyst. The anhydride inserts randomly into carbon-oxygen bonds of the polyether to generate ester bonds in the resulting polyetherester resin. The polyetherester resin is then combined with a vinyl monomer, preferably styrene, and is cured to produce a polyetherester thermoset.

We later found that, in addition to Lewis acids, protic acids that have a pKa less than about 0 and metal salts thereof will catalyze the insertion of an anhydride into the polyether to produce a polyetherester (see U.S. Pat. No. 5,436,313). We also discovered that these strong protic acids and their metal salts will catalyze the insertion of a carboxylic acid into a polyether (see U.S. Pat. No. 5,436,314).

The ability to make polyetheresters by randomly inserting anhydrides and carboxylic acids into polyethers provides a valuable way to make many unique polyetherester intermediates. While the processes described in our earlier patents provide valuable synthetic routes to polyetherester resins, some disadvantages are apparent.

One disadvantage of the conventional process for making polyetherester resins (i.e., insertion of an anhydride or a carboxylic acid into a polyether) is that resin yields are lower than desirable, typically in the low 80% range. In addition, the conventional process produces a significant waste stream of by-products. A process that would improve yields and reduce by-product generation is needed.

Product consistency of polyetherester resins is often less than satisfactory because significant and often unpredictable amounts of volatile anhydride can be lost overhead during manufacture, particularly if the reaction process is not closely monitored. A more forgiving process would be a bonus.

In the conventional process for making polyetherester resins, some water is often included to convert some or all of the anhydride to dicarboxylic acid prior to insertion. The added water introduces processing difficulties. For example, if refluxing water is not removed efficiently, heat-up time can be delayed undesirably, which sometimes requires addition of extra catalyst. In addition, the dicarboxylic acid produced (by hydrolysis or hydrolysis and isomerization) may be insoluble in the reaction mixture, causing mixing and sampling concerns. Preferably, the delay in heat-up would be avoided, and the mixture would remain homogeneous.

Polyetherester resins made the conventional way usually have higher color than is desirable. APHA color values are typically greater than 150. Lower color products can be made, but only by using undesirably longer reaction times. Low color can be important for many thermoset applications, particularly coatings. Thus, a way to make polyetherester resins with lower color is desirable.

Products with acid numbers less than about 45 mg KOH/g are hard to make using the conventional process. For some end uses, particularly molding and corrosion-resistant applications, polyetherester resins with lower acid numbers are needed. A process that would allow simple manufacture of polyetherester resins with low acid numbers would be valuable.

Water resistance is an important property of thermosets made from polyester and polyetherester resins. Exposure to harsh environments such as aqueous acid or caustic solutions causes these thermosets to deteriorate. In particular, the thermosets rapidly lose flexural strength, hardness, and surface integrity upon exposure to aqueous solutions. High-performance polyester resins such as iso resins were developed largely in response to demand for thermosets with better water resistance. Unfortunately, these high-performance resins are relatively expensive. The industry would benefit from new ways to improve water resistance of polyetherester resin-based thermosets, particularly ways that avoid expensive starting materials such as isophthalic acid.

In sum, an improved process for making polyetherester resins is needed. Preferably, the process would improve yields and product consistency, and would reduce by-product generation. A valuable process would also overcome processing difficulties that water addition creates, such as delayed heat-up times and heterogeneous reaction mixtures. Preferably, the process would make it possible to produce resins with low color or low acid numbers. A preferred process would give polyetherester resins that contribute good physical properties, including good water resistance, to thermosets made from the resins.

SUMMARY OF THE INVENTION

The invention is an improved process for making a polyetherester resin. The process comprises reacting a polyether with a diol diester in the presence of a catalyst that promotes random insertion of the diester into carbon-oxygen bonds of the polyether to produce the polyetherester resin.

While the conventional way to make polyetherester resins inserts an anhydride or a dicarboxylic acid into the polyether, I surprisingly found that insertion of a diol diester instead offers unexpected and valuable benefits. The process of the invention offers higher resin yields, reduced by-product generation, and the ability to make resins with low color and low acid numbers. In addition, the invention avoids the processing difficulties of water addition and gives products with better consistency. Finally, polyetherester resins made by the process contribute good physical properties, including good water resistance, to thermosets made from the resins.

DETAILED DESCRIPTION OF THE INVENTION

The process of the invention comprises reacting a polyether with a diol diester in the presence of a catalyst that promotes random insertion of the diester into carbon-oxygen bonds of the polyether to produce a polyetherester resin.

Polyethers suitable for use in the invention are those derived from base or acid-catalyzed ring-opening polymerization of cyclic ethers such as epoxides, oxetanes, oxolanes, and the like, and mixtures thereof. The polyethers have oxyalkylene repeat units (—O—A—) in which A has from 2 to 10 carbon atoms, preferably from 2 to 4 carbon atoms. The polyethers can have different end groups, depending upon how the polyethers are made or modified. For example, the polyether can have hydroxyl, ester, ether, acid, or amino end groups, or the like, or combinations thereof. Mixtures of different types of polyethers can be used.

Preferred polyethers for use in the process of the invention are polyether polyols. Suitable polyether polyols include, for example, polyoxypropylene polyols, polyoxyethylene polyols, ethylene oxide-propylene oxide copolymers, polytetramethylene ether glycols, and the like, and mixtures thereof. Typically, the polyols have average hydroxyl functionalities from about 2 to about 8, and number average molecular weights from about 250 to about 25,000. Preferred polyether polyols have an average hydroxyl functionality within the range of 5 about 2 to about 6, a hydroxyl number within the range of about 28 to about 260 mg KOH/g, and a number average molecular weight within the range of about 400 to about 12,000. Particularly preferred are polyoxypropylene diols and triols having a number average molecular weight within the range of about 1000 to about 4000. Other examples of suitable polyols appear in U.S. Pat. No. 5,319,006, the teachings of which are incorporated herein by reference.

The process inserts a diol diester into the polyether. By "diol diester" we mean reaction products of about 2 moles of a cyclic anhydride with about 1 mole of a diol. The diol diesters have two internal ester units, and two carboxylic acid end groups that result from ring opening of the cyclic anhydride. Suitable diol diesters can be made in other ways well known to those skilled in the art. For example, the diol can be esterified with a dicarboxylic acid or reacted with an acid halide. However, the anhydride route is most convenient.

Preferred diol diesters have the general formula:

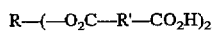

in which R is a bivalent $C_2$–$C_{30}$ alkyl or aralkyl moiety derived from a diol, and R' is a bivalent $C_2$–$C_{20}$ alkyl or aryl moiety derived from a cyclic anhydride.

Suitable diol diesters derive from $C_2$–$C_{30}$ diols, including, for example, ethylene glycol, propylene glycol, diethylene glycol, dipropylene glycol, triethylene glycol, tripropylene glycol, 2-methyl-1,3-propanediol, neopentyl glycol, 1,4-butanediol, 1,6-hexanediol, 1,4-benzenedimethanol, 1,4-cyclohexane-dimethanol, bisphenol A, bisphenol F, alkoxylated bisphenols, and the like, and mixtures thereof. Suitable cyclic arthydrides from which the diol diesters derive am saturated or unsaturated $C_4$–$C_{20}$ cyclic arthydrides. Examples include maleic anhydride, phthalic arthydride, succinic anhydride, itaconic arthydride, citraconic arthydride, trimellitic anhydride, and the like, and mixtures thereof.

The amount of diol diester used depends on many factors, including which diol diester is used, the type of polyetherester resin desired, the target molecular weight of the polyetherester, the amount of unsaturation desired in the resin, and other factors. Generally, the amount of diol diester used is within the range of about 20 to about 80 wt. % based on the combined amount of polyether and diol diester used to make the polyetherester resin. A more preferred range is from about 30 to about 70 wt. %; most preferred is the range from about 40 to about 60 wt. %.

Preferably, only a diol diester is used; however, relatively minor proportions of arthydrides and/or carboxylic acids are optionally included in the process. Examples of suitable anhydrides and dicarboxylic acids that may be used appear in U.S. Pat. Nos. 5,436,313 and 5,436,314, the teachings of which are incorporated herein by reference.

The process of the invention uses an "insertion catalyst" to promote random insertion of the diol diester into the polyether. Suitable insertion catalysts for diol diesters are the ones previously described for insertion of anhydrides and dicarboxylic acids into polyethers. They include Lewis acids, protic acids that have a pKa less than about 0, and metal salts of the protic acids. The insertion catalyst is used in an amount effective to promote random insertion of the diol diester into carbon-oxygen bonds of the polyether to produce a polyetherester resin.

Preferred Lewis acids are metal halides of the formula $MX_n$, wherein M is a metal having an oxidation number from 2 to 4, X is a halogen, and n is an integer from 2 to 4. Examples of suitable Lewis acids are zinc chloride, zinc bromide, stannous chloride, stannous bromide, aluminum chloride, ferric chloride, boron trifluoride, and the like, and mixtures thereof. Most preferred are zinc chloride and zinc bromide. When a Lewis acid catalyst is used, it is preferred to use an amount within the range of about 0.01 to about 5 wt. % based on the amount of polyether. Additional examples of suitable Lewis acids are found in U.S. Pat. No. 5,319,006, the teachings of which are incorporated herein by reference.

Protic acids (organic and inorganic) that have a pKa less than about 0 are also useful as insertion catalysts. Generally, the acids will be stronger than organic carboxylic acids. Suitable acids include arylsulfonic acids, alkylsulfonic acids, and halogenated alkyl- and arylsulfonic acids. Also suitable are hydrogen halides, halosulfonic acids, tetrafluoroboric acid, heteropolyacids, and sulfuric acid. Mixtures of different acids can be used. Examples include p-toluenesulfonic acid, trifluoromethanesulfonic acid (triflic acid), trichloromethanesulfonic acid, hydrochloric acid, phosphotungstic acid, and the like. Preferred protic acids are sulfuric acid, p-toluenesulfonic acid, and phosphotungstic acid. When a protic acid is used as the catalyst, it is generally preferred to use an amount within the range of about 0.01 to about 1 wt. % based on the amount of polyether. A more preferred range is from about 0.01 to about 0.3 wt. %. Additional examples of suitable protic acids are found in U.S. Pat. No. 5,436,313, the teachings of which are incorporated herein by reference.

Metal salts derived from protic acids that have a pKa less than about 0 are also effective insertion catalysts. Preferred salts are metal salts of arylsulfonic acids, alkylsulfonic acids, halogenated aryl- and alkylsulfonic acids, tetrafluoroboric acid, sulfuric acid, heteropolyacids, and halosulfonic acids. Sulfonic acid salts, especially triflate salts, are particularly preferred. Preferably, the metal is selected from Group IA, IIA, IIB, IB, IIIA, IVA, VA, and VIII. Thus, the metal can be, for example, lithium, potassium, magnesium, zinc, copper, aluminum, tin, antimony, iron, nickel. Examples of suitable metal salts are lithium triflate, sodium triflate, magnesium triflate, zinc triflate, copper(II) triflate, zinc tetrafluoroborate, zinc p-toluenesulfonate, aluminum triflate, iron(II) tetrafluoroborate, tin(II) triflate, and the like, and mixtures thereof. When a metal salt is used as the catalyst, it is preferably used in an amount within the range of about 1 part per million ($10^{-4}$ wt. %) to about 1 wt. % based on the amount of polyether. A more preferred range is from about 0.01 wt. % to about 0.3 wt. %. Additional examples of suitable metal salts of protic acids are found in U.S. Pat. No. 5,436,313, the teachings of which are incorporated herein by reference.

Any convenient temperature can be used to make polyetheresters by the process of the invention provided that the temperature suffices to promote insertion of the diol diester into the polyether. Generally, however, the reaction is too slow to be practical at temperatures below about 60° C.

Preferably, the process is performed at a temperature within the range of about 80° C. to about 250° C. A more preferred range is from about 100° C. to about 220° C.; most preferred is the range from about 150° C. to about 200° C.

The process is conveniently performed by combining the polyether, diol diester, catalyst, and any optional components (anhydrides, carboxylic acids) in any desired order or manner, and heating the mixture at a temperature that promotes insertion of the diol diester into the polyether to produce a polyetherester resin. The progress of the reaction can be followed by measuring the acid number, which will decrease and level off as the reaction proceeds.

One way to perform the process of the invention is to first prepare and isolate the diol diester. A second reactor is then charged with diol diester, polyether, and insertion catalyst, and the mixture is heated to produce the polyetherester resin. Examples 1 and 2 below illustrate this procedure ("Method A").

The polyetherester resin can also be made in the same reactor that was used to make the diol diester. Following preparation of the diol diester, the insertion catalyst and polyether are introduced into the same reactor, and the polyetherester resin is made. Examples 5 and 6 illustrate this technique ("Method B").

In a third variation, the diol diester is prepared in the presence of the polyether. The diol and anhydride used to make the diol diester react in the polyether at a temperature high enough to produce a mixture of diol diester in polyether, but low enough to avoid insertion of the anhydride or the diol diester into the polyether. After diol diester preparation is complete, the reaction temperature is increased to promote insertion of the diol diester into the polyether to make the polyetherester resin. Examples 7–13 below illustrate this approach ("Method C").

As noted earlier, the process of the invention has many advantages compared with the conventional process for making polyetheresters by insertion of an anhydride or a carboxylic acid into a polyether. First, the process gives higher yields of polyetherester resin products. While the conventional process gives yields in the 75–80% range (see Comparative Examples 3 and 4), yields from the process of the invention typically hit 85–90% or better (see Examples 2 and 5–13).

Second, the process of the invention reduces organic by-product generation and waste-disposal costs associated with organic by-products (see Example 2 and Comparative Examples 3–4).

Third, the process gives polyetherester resins with low color. Polyetherester resins made the conventional way usually have APHA color values greater than 150. Lower color products can be made, but much longer reaction times are needed. Because low color is important for coating applications, a process that gives a resin with low color is valuable. As Example 2 shows, the process gives a resin with reduced color.

Fourth, the process of the invention makes it easier to produce polyetheresters having low acid numbers. Products with acid numbers less than about 45 mg KOH/g are hard to make using the conventional process. However, for molding and corrosion-resistant applications, polyetherester resins with low acid numbers are needed. As Examples 7–13 (see Table 1) demonstrate, resins with acid numbers in the 30–40 mg KOH/g range are routinely made with the process of the invention. Example 14 and Comparative Example 15 show that the diol diester insertion process gives an intermediate that can be successfully chain extended with a primary diol to make a low-acid-number polyetherester resin. In contrast, attempts to make a low-acid-number product by chain extension when the resin is made by the conventional method (i.e., insertion of anhydride into polyether) can result in gellation.

Fifth, the process avoids processing difficulties of water addition. Water is often added in a conventional process to convert maleic anhydride to maleic acid. Isomerization of maleic acid to fumaric acid under the reaction conditions results in a heterogeneous reaction mixture, which is preferably avoided because sampling becomes less consistent and mixing becomes more difficult. Water addition can cause other problems. Refluxing water prolongs heat-up time undesirably, and sometimes makes addition of extra catalyst necessary. The process of the invention circumvents these issues by not adding water.

Finally, the process of the invention permits better product consistency. Significant and often unpredictable overhead losses of volatile anhydride can plague the conventional manufacturing process, particularly if the reaction process is not closely monitored. In contrast, the process of the invention is more forgiving. The diol diesters are much less volatile than the anhydrides normally used, and they tend to stay in the reaction mixture even at elevated temperatures.

Polyetherester resins made by the process of the invention commonly have a large proportion of carboxylic acid end groups. The polyetherester can be heated with a glycol such as propylene glycol, dipropylene glycol, or the like, (typically 5–10 wt. %) to esterify these acid groups and produce glycol-capped polyetheresters that have hydroxyl end groups.

Alternatively, the polyetherester resin can be reacted with a chain extender, preferably a primary diol or a diepoxy compound, to produce a chain-extended polyetherester resin as is taught in copending Appl. Ser. No. 08/608,379, filed Feb. 28, 1996, now allowed. Reaction with a primary diol or diepoxy compound results in a substantial increase in the weight average molecular weight of the resin. We found that these chain-extended resins are useful in making high-performance polyetherester thermosets with excellent water resistance.

Suitable primary diols have two primary hydroxyl groups (—$CH_2OH$) available for reaction with the acid groups of the polyetherester resin. Preferred primary diols are $C_2$–$C_{10}$ diols, including, for example, ethylene glycol, 2-methyl-1, 3-propanediol, neopentyl glycol, diethylene glycol, triethylene glycol, 1,4-butanediol, 1,6-hexanediol, 1,4-cyclohexanedimethanol, 1,4-benzenedimethanol, and the like, and mixtures thereof. Preferably, the amount of primary diol used will be within the range of about 1 to about 20 wt. %.

Suitable diepoxy compounds have two epoxy groups available for reaction with the carboxylic acid groups of the polyetherester resin. Epoxy resins, such as bisphenol A diglycidyl ether, are preferred diepoxy compounds. Suitable epoxy resins include Shell Chemical's "EPON" resins such as EPON 828 resin, and Dow Chemical's "D.E.R." resins, such as D.E.R. 330 and D.E.R. 331 resins. Other suitable diepoxy compounds are taught in copending Appl. Ser. No. , filed Feb. 28, 1996 now allowed. Usually, at least about 1 wt. % of diepoxy compound is used based on the amount of polyetherester resin, Preferably, the diepoxy compound is used in an amount within the range of about 5 to about 60 wt. %.

Polyetherester resins made by the process of the invention can be formulated into polyetherester thermosets by reacting the resins with a vinyl monomer in the presence of a free-radical initiator.

Vinyl monomers suitable for use in the invention include, for example, vinyl aromatic monomers, vinyl esters of carboxylic acids, acrylic and methacrylic acid esters, acrylamides and methacrylamides, acrylonitrile and methacrylonitrile, alkyl vinyl ethers, allyl esters of aromatic di- and polyacids, and the like, and mixtures thereof. Preferred vinyl monomers are vinyl aromatic monomers, methacrylic acid esters, and diallyl esters of aromatic di- and polyacids. Particularly preferred vinyl monomers are styrene, vinyl toluene, methyl methacrylate, and diallyl phthalate. Generally, the amount of vinyl monomer used will be within the range of about 10 to about 70 wt. % based on the amount of cured polyetherester thermoset; a more preferred range is from about 20 to about 65 wt. %.

Free-radical initiators useful in the invention are any of the peroxide and azo-type initiators that are well known in the art for curing conventional unsaturated polyester resins. Peroxide initiators are preferred. Suitable examples include benzoyl peroxide, methyl ethyl ketone peroxide, tert-butylperbenzoate, AIBN, and the like. The amount of free-radical initiator used will typically be within the range of about 0.1 to about 5 wt. % based on the weight of cured polyetherester thermoset.

Fillers, glass fibers, pigments, or other additives may be included in the polyetherester thermosets of the invention. Suitable fillers include, for example, talc, calcium oxide, calcium carbonate, aluminum trihydrate, magnesium silicate, alumina, carbon, clays, diatomaceous earth, and the like. Glass powder, spheres, fibers, or chopped glass of any size or shape can be used to reinforce the polyetherester thermoset.

The polyetherester thermosets are made by reacting the polyetherester resin, vinyl monomer, and free-radical initiator according to methods well known in the art of making thermosets from unsaturated polyester resins. Typically, a resin mixture that contains vinyl monomer is combined with the free-radical initiator at room or elevated temperature, and is cured to give a solid product that may be post-cured if desired by heating at elevated temperature. The examples below illustrate suitable procedures for making the thermosets.

The process of the invention gives polyetherester resins that perform well in thermoset applications. As Table 2 shows, thermosets made from these polyetherester resins exhibit a favorable balance of physical properties. Water resistance of the thermosets, as evaluated by the percent retention of flexural strength following exposure to boiling water for six days, is typically in the 70–85% range.

The following examples merely illustrate the invention. Those skilled in the art will recognize many variations that are within the spirit of the invention and scope of the claims.

EXAMPLE 1

Preparation of 2-Methyl-1,3-propanediol Bis-Maleate

A three-liter resin kettle equipped with mechanical stirrer, nitrogen sparge tube, and addition funnel is charged with maleic anhydride (1713 g, 17.3 mol). The anhydride is heated to 60° C. to melt it. 2-Methyl-1,3-propanediol (787 g, 8.73 mol) is added at a rate effective to keep the exothermic reaction mixture at a temperature less than about 100° C. Following diol addition, the mixture is heated at 85° C. for another 2 h. The product (2475 g, 99% yield) is a clear, viscous liquid. Analysis by $^1H$ and $^{13}C$ NMR spectroscopy indicates that the product is the desired 2:1 adduct of maleic anhydride and 2-methyl-1,3-propanediol.

The same general procedure is used to make a bis-maleate from propylene glycol. 2-Methyl-1,3-propanediol bis-maleate and propylene glycol bis-maleate are used to make polyetherester resins by insertion of the bis-maleate into a polyether polyol as is described below.

EXAMPLE 2

Preparation of a Polyetherester Resin from a Polyether Triol and 2-Methyl-1,3-propanediol Bis-maleate (Method A)

A twelve-liter reaction vessel equipped with mechanical stirrer, thermocouple, nitrogen sparge tube, and reflux condenser is charged with a 3000 molecular weight polyoxypropylene triol (3430 g), 2-methyl-1,3-propanediol bis-maleate (3570 g, prepared as in Example 1), and p-toluenesulfonic acid (7.0 g). The mixture is heated at 190° C. with stirring and nitrogen sparging for 5 h to reach an acid number of 102 mg KOH/g. Propylene glycol (271 g) is added, and heating continues for another 5 h to reach an acid number of 53 mg KOH/g. The product (6444 g, 88.6%) is a polyetherester resin resulting from random insertion of diol bis-maleate into C-O bonds of the polyether polyol. Water and organic by-products (674 g, 9.3 %) are also collected. The polyetherester resin is blended with 40 wt. % styrene. The blend has viscosity=500 cps and APHA color=80.

COMPARATIVE EXAMPLE 3

Preparation of a Polyetherester Resin from a Polyether Triol and Maleic Anhydride A twelve-liter reaction vessel equipped as in Example 2 is charged with a 3000 molecular weight polyoxypropylene triol (5000 g) and maleic anhydride (2692 g). The mixture is heated to about 70° C. to melt the anhydride. A solution of p-toluenesulfonic acid (7.7 g) in water (494 g) is added. The mixture is heated to 190° C. with stirring and nitrogen sparging for 7.5 h to reach an acid number of 133 mg KOH/g. Propylene glycol (500 g) is added, and heating continues for another 5 h to reach an acid number of 55 mg KOH/g. The polyetherester product (6501 g, 78%) is collected, along with water and organic by-products (1888 g, 22%). The polyetherester resin is blended with 40 wt. % styrene. The blend has viscosity=280 cps and APHA color= 150.

COMPARATIVE EXAMPLE 4

Preparation of a Polyetherester Resin from a Polyether Triol and Maleic Anhydride The procedure of Comparative Example 3 is generally followed, except that when the acid number reaches 134 mg KOH/g, 2-methyl-1,3-propanediol (494 g) is added. The reaction continues until the acid number drops to 47 mg KOH/g. Upon cooling, the product (6551 g, 82%) is collected and analyzed (see Table 1).

The results in Example 2 and Comparative Examples 3 and 4 show that a resin made from a diol bis-maleate is produced in higher overall yield (89% vs. 79–82%) and with less water and organic by-products (9 wt. % vs. 18–21 wt. %) compared with a polyetherester made from maleic anhydride. In addition, the resin made from the bis-maleate has a lower APHA color (80 vs. 150).

EXAMPLE 5

Preparation of a Polyetherester Resin from Propylene Glycol Bis-maleate One-Pot Procedure (Method B)

This example shows how to make a polyetherester resin from a bis-maleate in which the bis-maleate is prepared in the same reaction vessel before introducing a polyether polyol and insertion catalyst.

A three-liter reactor equipped as in Example 2 is charged with maleic anhydride (874 g), which is melted by heating to 70° C. Propylene glycol (339 g) is added, and the exothermic reaction is maintained at 130° C. or less until the reaction subsides (about 2 h). The acid number of this bisomaleate intermediate is 448 mg KOH/g. A 3000 mol. wt. polyoxypropylene triol (1225 g) and p-toluenesulfonic acid (2.4 g) are added, and the mixture is heated at 190° C. until the acid number drops to 102 mg KOH/g. Propylene glycol (92 g) is added, and heating continues until the acid number reaches 59 mg KOH/g. The product is cooled and isolated (2165 g, 87% yield). Gel permeation chromatography (GPC) analysis shows: Mn=1450, Mw=7590. A blend of the resin with 40 wt. % styrene has APHA color=65.

EXAMPLE 6

Preparation of a Polyetherester Resin from Propylene Glycol Bis-maleate/phthalate One-Pot Procedure (Method B)

A three-liter reactor equipped as described in Example 2 is charged with a mixture of maleic anhydride (750 g) and phthalic anhydride (250 g), which is melted by heating to 70° C. Propylene glycol (348 g) is added, and the exothermic reaction is maintained at 130° C. or less until the reaction subsides (about 2 h). The acid number of this bis-maleate/phthalate intermediate is 417 mg KOH/g. A 3000 mol. wt. polyoxypropylene triol (1152 g) and p-toluenesulfonic acid (2.5 g) are added, and the mixture is heated at 190° C. until the acid number drops to 123 mg KOH/g. Propylene glycol (237 g) is added, and heating continues until the acid number reaches 42 mg KOH/g. The product is cooled and isolated (2372 g, 89% yield). GPC analysis shows: Mn =1475, Mw=7590. A blend of the resin with 40 wt. % styrene has APHA color =150.

EXAMPLES 7–13

Preparation of Polyetherester Resins from Diol Bis-maleates:

In-Polyol Preparation of the Bis-maleate (Method C) and Thermosets from the Resins In each of these examples, a bis-maleate is prepared in the presence of the polyether polyol. Initially, the anhydride and glycol react to make a bis-maleate. When the reaction mixture reaches about 150° C. or greater, the bis-maleate inserts into the polyether polyol to make the polyetherester resin. A twelve-liter reactor equipped as in Example 2 is charged with maleic anhydride (2692 g) and a 3000 mol. wt. polyoxypropylene triol (3956 g). The mixture is heated to 75° C. to melt the anhydride. Propylene glycol or 2-methyl-1,3-propanediol (see Table 1 for amounts) is added, along with p-toluenesulfonic acid (2.4 g). A mixture of bis-maleate and polyol forms. Insertion of the bis-maleate begins as the temperature rises. The mixture is heated at 190° C. until the acid number reaches 80–100 mg KOH/g. Propylene glycol or 2-methyl-1,3-propanediol (see Table 1 for amounts) is added, and heating continues until the acid number reaches about 30–40 mg KOH/g. The product is cooled and isolated (see Table 1 for % yields, acid numbers, APHA colors, and GPC results).

The resins are diluted to 40% styrene content, and are used to make polyetherester thermosets as described below.

The resins are cured using 0.12 wt. % of cobalt naphthenate solution (6% Co naphthenate in mineral spirits) and 1.2 wt. % of LUPERSOL DDM9 initiator (methyl ethyl ketone peroxide, product of Atochem) at room temperature overnight, followed by a post-cure at 100° C. for 5 h. Properties of the cured thermosets, including results of 6-day water-boil testing, appear in Table 2.

EXAMPLE 14

Preparation of a Low-Acid-Number Polyetherester Resin

A twelve-liter reactor equipped as in Example 2 is charged with maleic anhydride (2692 g) and a 3000 mol. wt. polyoxypropylene triol (5000 g). The mixture is heated to 75° C. to melt the anhydride, and a mixture of propylene glycol (1044 g) and p-toluenesulfonic acid (2.4 g) is added. A mixture of bis-maleate and polyol forms. Insertion of the bis-maleate begins as the temperature rises. The mixture is heated at 190° C. until the acid number reaches 99 mg KOH/g. 2-Methyl-1,3-propanediol (494 g) is added, and heating continues until the acid number reaches about 21 mg KOH/g. The product is cooled and isolated (6998 g, 88%). GPC results: Mn=4263, Mw=59,990.

COMPARATIVE EXAMPLE 15

Attempted Preparation of a Low-Acid-Number Polyetherester Resin

A twelve-liter reactor equipped as in Example 2 is charged with maleic anhydride (2692 g) and a 3000 mol. wt. polyoxypropylene triol (5000 g). The mixture is heated to 75° C. to melt the anhydride, and a solution of p-toluenesulfonic acid (7.7 g) in water (494 g) is added. The mixture is heated at 190° C. until the acid number reaches 118 mg KOH/g. 2-Methyl-1,3-propanediol (740 g) is added, and heating continues until the acid number reaches about 33 mg KOH/g. Upon cooling, the product gels into a gelatinous, insoluble mass that is not suitable for use in formulating a polyetherester thermoset.

COMPARATIVE EXAMPLE 16

Preparation of a Low-Acid-Number Polyetherester Resin

A twelve-liter reactor equipped as in Example 2 is charged with maleic anhydride (2692 g) and a 3000 mol. wt. polyoxypropylene triol (5000 g). The mixture is heated to 75° C. to melt the anhydride, and a solution of p-toluenesulfonic acid (7.7 g) in water (494 g) is added. The mixture is heated at 190° C. until the acid number reaches 128 mg KOH/g. Propylene glycol (390 g) is added, and heating continues until the acid number reaches 88 mg KOH/g. 2-Methyl-1,3-propanediol (410 g) is added, and heating continues until the acid number reaches about 29 mg KOH/g. The product is cooled and isolated (6734 g, 82%). GPC results: Mn=1860, Mw=22,130.

This example shows that it is possible to prepare a low-acid-number resin by first capping a conventionally prepared resin with propylene glycol, and then chain extending it with 2-methyl-1,3-propanediol; however, the % yield of polyetherester resin is still significantly lower (low 80s) than the yield from the process of the invention (high 80s).

EXAMPLE 17

Preparation of a Low-Acid-Number Resin: Use of Water and Glycol

A three-liter reactor equipped as in Example 2 is charged with maleic anhydride (583 g) and a 3000 mol. wt. polyoxypropylene triol (948 g). The mixture is heated to 75° C. to melt the anhydride, and a solution of p-toluenesulfonic acid (1.7 g) in water (53 g) and propylene glycol (135 g) is added. The mixture is heated at 190° C. until the acid number reaches 114 mg KOH/g. 2-Methyl-1,3-propanediol (130 g) is added, and heating continues until the acid number reaches 29 mg KOH/g. The product is cooled and isolated (1526 g, 87%). GPC results: Mn=2331, Mw=34,060. A blend of the resin with 40 wt. % styrene has APHA color=60.

EXAMPLE 18

Preparation of an Epoxy-Extended Polyetherester Resin

A twelve-liter reactor equipped as in Example 2 is charged with maleic anhydride (3400 g) and a 2000 MW polyoxypropylene diol (5282 g). The mixture is heated to 75° C. to melt the anhydride, and a mixture of p-toluenesulfonic acid (10 g) and propylene glycol (1318 g) is added. The mixture is heated at 190° C. until the acid number reaches 103 mg KOH/g. The reaction mixture is cooled to 160°C., and EPON 828 resin (product of Shell Chemical, 1588 g) is added. The reaction temperature is maintained at 150° C. until the acid number reaches 53 mg KOH/g. After cooling, 10,450 g (91.4% yield) of resin is isolated. GPC results: Mn=1463, Mw=7341.

EXAMPLE 19

Preparation of a Polyetherester Resin from Propylene Glycol Bis-maleate/succinate A three-liter reactor equipped as in Example 2 is charged with maleic anhydride (690 g) and succinic anhydride (230 g). The mixture is heated to 75° C. to melt the maleic anhydride, and propylene glycol (353 g) is added. The exothermic reaction is maintained at or below 130° C. for two hours. A 3000 mol. wt. polyoxypropylene triol (1027 g) and p-toluenesulfonic acid (2.3 g) are added. The mixture is heated at 190° C. until the acid number falls to 112 mg KOH/g. Propylene glycol (146 g) is added, and heating continues until the acid number is 38 mg KOH/g. After cooling, 2077 g (86.8% yield) of resin is collected. GPC results: Mn=1982, Mw=10,730. A blend of the resin with 40% styrene has APHA color=65.

The preceding examples are meant only as illustrations; the following claims define the scope of the invention.

TABLE 1

Polyetherester Resins from Diol Bis-Maleates (Method C)

| Ex # | Bis-maleate | Amt. of diol in bis-maleate (g) | First stage acid # (mg KOH/g) | Chain extender | Amt. of extender (g) | Final acid # (mg KOH/g) | APHA color | Resin % yield | Mn | Mw/Mn |
|---|---|---|---|---|---|---|---|---|---|---|
| 7 | PG | 1044 | 96 | PG | 437 | 37 | 130 | 87 | 1230 | 9.1 |
| 8 | PG | 1044 | 89 | PG | 359 | 41 | 100 | 88 | 1590 | 6.4 |
| 9 | PG | 1044 | 80 | PG | 281 | 41 | — | 86 | 1320 | 28 |
| 10 | PG | 1044 | 101 | MPD | 432 | 28 | 85 | 87 | 2410 | 11 |
| 11 | PG | 1044 | 82 | MPD | 308 | 33 | — | 86 | 1940 | 26 |
| 12 | MPD | 1236 | 102 | MPD | 432 | 32 | 90 | 87 | 1700 | 10 |
| 13 | MPD | 1236 | 80 | MPD | 308 | 31 | 120 | 89 | 3090 | 12 |
| C3 | * | * | 133 | PG | 500 | 49 | 150 | 81 | 1600 | 6.3 |
| C4 | * | * | 137 | MPD | 494 | 47 | — | 82 | — | — |

The polyetherester resins of Examples 7–13 are made by Method C, i.e., the bis-maleate is made in the presence of the polyether polyol.
PG = propylene glycol; MPD = 2-methyl-1,3-propanediol
*No bis-maleate is used; instead, the polyetherester resin is prepared in conventional manner from maleic anhydride and polyether triol.

TABLE 2

Thermosets from Polyetherester Resins

| Ex # | Bis-meleate | Chain extender | Tensile strength (psi) | Elongation (%) | Flexural strength (kpsi) | DTUL (°F.) | Flexural strength retained (%) |
|---|---|---|---|---|---|---|---|
| 7 | PG | PG | 7390 | 4.6 | 13.5 | 215 | 46 |
| 8 | PG | PG | 7150 | 3.4 | 13.9 | 216 | 27 |
| 9 | PG | PG | 7560 | 3.1 | 15.3 | 225 | 74 |
| 10 | PG | MPD | 6840 | 3.7 | 12.6 | 219 | 70 |
| 11 | PG | MPD | 8330 | 4.3 | 15.0 | 222 | 84 |
| 12 | MPD | MPD | 6660 | 2.5 | 13.4 | 222 | 83 |
| 13 | MPD | MPD | 4650 | 1.5 | 12.5 | 221 | 80 |
| C3 | * | PG | 7170 | 3.1 | 14.1 | 213 | 26 |
| C4 | * | MPD | 6300 | 2.3 | 11.4 | 226 | 74 |

*No bis-maleate is used; instead, the polyetherester resin is prepared in conventional manner from maleic anhydride and polyether triol.
PG = propylene glycol; MPD = 2-methyl-1,3-propanediol
Flexural strength retention (%) is determined by measuring flexural strength of fully cured thermoset samples before and after exposure for 6 days to boiling water.

I claim:

1. A process for making a polyetherester resin, said process comprising reacting a polyether with a diol diester in the presence of a catalyst that promotes random insertion of the diester into carbon-oxygen bonds of the polyether to produce the polyetherester resin.

2. The process of claim 1 wherein the polyether is a polyether polyol having an average hydroxyl functionality within the range of about 2 to about 6, a hydroxyl number within the range of about 28 to about 260 mg KOH/g, and a number average molecular weight within the range of about 400 to about 12,000.

3. The process of claim 1 wherein the polyether is a polyether diol or triol having a number average molecular weight within the range of about 1000 to about 4000.

4. The process of claim 1 wherein the diol diester is the reaction product of about 2 moles of a cyclic anhydride and about 1 mole of a diol, and has the general formula:

in which R is a bivalent $C_2$–$C_{30}$ alkyl or aralkyl moiety derived from the diol, and R' is a bivalent $C_2$–$C_{20}$ alkyl or aryl moiety derived from the cyclic anhydride.

5. The process of claim 4 wherein the diol is selected from the group consisting of ethylene glycol, propylene glycol, diethylene glycol, dipropylene glycol, triethylene glycol, tripropylene glycol, 2-methyl-1,3-propanediol, neopentyl glycol, 1,4-butanediol, 1,6-hexanediol, 1,4-benzenedimethanol, 1,4-cyclohexanedimethanol, bisphenol A, bisphenol F, and alkoxylated bisphenols.

6. The process of claim 4 wherein the cyclic anhydride is selected from the group consisting of maleic anhydride, phthalic anhydride, succinic anhydride, itaconic anhydride, citraconic anhydride, and trimellitic anhydride.

7. The process of claim 1 wherein the insertion catalyst is selected from the group consisting of Lewis acids, protic acids that have a pKa less than about 0, and metal salts of the protic acids.

8. A polyetherester resin made by the process of claim 1.

9. A process for making a polyetherester thermoset, said process comprising reacting the polyetherester resin of claim 8 with a vinyl monomer in the presence of a free-radical initiator to produce the polyetherester thermoset.

10. The process of claim 9 wherein the vinyl monomer is styrene.

11. A polyetherester thermoset made by the process of claim 9.

12. The process of claim 1 wherein the polyetherester resin is further reacted with an extender selected from the group consisting of primary diols and diepoxy compounds to produce a chain-extended polyetherester resin.

13. A chain-extended polyetherester resin made by the process of claim 12.

14. A process for making a polyetherester thermoset, said process comprising reacting the chain-extended polyetherester resin of claim 13 with a vinyl monomer in the presence of a free-radical initiator to produce the polyetherester thermoset.

15. A polyetherester thermoset made by the process of claim 14.

16. A process for making a polyetherester resin, said process comprising reacting a polyether polyol with a diol bis-maleate in the presence of a catalyst that promotes random insertion of the bis-maleate into carbon-oxygen bonds of the polyether to produce the polyetherester resin.

17. The process of claim 16 wherein the diol bis-maleate is the reaction product of about 2 moles of maleic anhydride and about 1 mole of a diol selected from the group consisting of ethylene glycol, propylene glycol, diethylene glycol, dipropylene glycol, triethylene glycol, tripropylene glycol, 2-methyl-1,3-propanediol, neopentyl glycol, 1,4-butanediol, 1,6-hexanediol, 1,4-benzenedimethanol, 1,4-cyclohexanedimethanol, bisphenol A, bisphenol F, and alkoxylated bisphenols.

18. The process of claim 16 wherein the polyether polyol has an average hydroxyl functionality within the range of about 2 to about 6, a hydroxyl number within the range of about 28 to about 260 mg KOH/g, and a number average molecular weight within the range of about 400 to about 12,000.

19. The process of claim 16 wherein the polyether polyol is a diol or triol having a number average molecular weight within the range of about 1000 to about 4000.

20. The process of claim 16 wherein the insertion catalyst is selected from the group consisting of Lewis acids, protic acids that have a pKa less than about 0, and metal salts of the protic acids.

21. A polyetherester resin made by the process of claim 16.

22. A process for making a polyetherester thermoset, said process comprising reacting the polyetherester resin of claim 21 with styrene in the presence of a free-radical initiator to produce the polyetherester thermoset.

23. A polyetherester thermoset made by the process of claim 22.

24. 2-Methyl-1,3-propanediol bis-maleate.

25. A diol diester which comprises the reaction product of about 2 moles of a cyclic anhydride and about 1 mole of 2-methyl-1,3-propanediol, wherein the diol diester has the general formula:

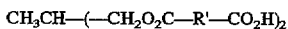

in which R' is a bivalent $C_2$–$C_{20}$ alkyl or aryl moiety derived from the cyclic anhydride.

* * * * *